(12) United States Patent
Zhang et al.

(10) Patent No.: US 11,317,791 B2
(45) Date of Patent: May 3, 2022

(54) SYSTEM AND METHOD FOR WIRELESS CAPSULE ENDOSCOPE WITH ADAPTIVE FRAME RATE

(71) Applicant: Ankon Technologies CO., LTD., Wuhan (CN)

(72) Inventors: Hao Zhang, Wuhan (CN); Hao Liu, Wuhan (CN); Peipei Xu, Wuhan (CN); Xinhong Wang, San Diego, CA (US); Xiaodong Duan, Pleasanton, CA (US); Guohua Xiao, Plano, TX (US)

(73) Assignee: ANKON TECHNOLOGIES CO., LTD., Shanghai (CN)

( * ) Notice: Subject to any disclaimer, the term of this patent is extended or adjusted under 35 U.S.C. 154(b) by 869 days.

(21) Appl. No.: 16/163,514

(22) Filed: Oct. 17, 2018

(65) Prior Publication Data

US 2019/0117049 A1   Apr. 25, 2019

(30) Foreign Application Priority Data

Oct. 19, 2017   (CN) .......................... 201710979327.1

(51) Int. Cl.
*A61B 1/04* (2006.01)
*A61B 1/00* (2006.01)
*A61B 1/045* (2006.01)
*A61B 34/20* (2016.01)

(52) U.S. Cl.
CPC .......... *A61B 1/041* (2013.01); *A61B 1/00006* (2013.01); *A61B 1/00036* (2013.01); *A61B 1/00108* (2013.01); *A61B 1/045* (2013.01); *A61B 2034/2046* (2016.02); *A61B 2560/0214* (2013.01)

(58) Field of Classification Search
CPC . A61B 1/041; A61B 1/00108; A61B 1/00029; A61B 1/00006; A61B 1/00036; A61B 1/00158; A61B 1/00147
See application file for complete search history.

(56) References Cited

U.S. PATENT DOCUMENTS

| | | | | |
|---|---|---|---|---|
| 2002/0173718 | A1* | 11/2002 | Frisch | A61B 5/073 600/424 |
| 2006/0184039 | A1* | 8/2006 | Avni | H04N 5/3696 600/476 |
| 2007/0225560 | A1* | 9/2007 | Avni | A61B 1/0684 600/118 |
| 2008/0242931 | A1* | 10/2008 | Nishino | A61B 5/065 600/117 |

* cited by examiner

*Primary Examiner* — Aaron B Fairchild
(74) *Attorney, Agent, or Firm* — Treasure IP Group, LLC

(57) ABSTRACT

The present invention discloses a system for wireless capsule endoscope with adaptive frame rate, comprising: a recorder data processor to filter the first posture information of a capsule endoscope and the second posture information of a portable recorder to obtain a quaternion $p_0$ of the first posture information and a quaternion $p_1$ of the second posture information, and to calculate an interpolated median $s_0$ between $p_0$ and $p_1$ at time $t_0$, and an interpolated median $s_1$ between $p'_0$ and $p'_1$ at time $t_1$; the recorder data processor also calculates a difference $diff_0$ between the interpolated median $s_0$ and $s_1$, and works out the dot product of the difference $diff_0$ and unit quaternion [1, 0, 0, 0].

10 Claims, 1 Drawing Sheet

SYSTEM AND METHOD FOR WIRELESS CAPSULE ENDOSCOPE WITH ADAPTIVE FRAME RATE

CROSS REFERENCE TO RELATED APPLICATIONS

This application claims priority to Chinese Patent Application No. 201710979327.1 filed on Oct. 19, 2017, the contents of which are incorporated by reference herein.

TECHNICAL FIELD

The present invention relates to the technical field of medical apparatus and instruments, in particular to a system and a method for a wireless capsule endoscope with adaptive frame rate.

BACKGROUND OF THE INVENTION

Capsule endoscopes have been widely used in digestive tract examination because of their non-invasion, no pain, safety and high reliability etc. A capsule endoscope takes photos inside the examinee mainly relying on an internal camera unit, and the images taken would be compressed with a data processor and wirelessly transmitted to a recorder outside of the body. All of the devices are powered by an internal battery in the capsule. The capsule takes about 50,000 photos during a complete examination. But, there are often many repeated images which may not only waste the limited power of the capsule but also increase reading workload of the physician. Therefore, it is necessary to invent a method to reduce the number of repeated and invalid images, improve operating efficiency of the capsule, and save power of the capsule, thereby to reduce the number of images the physicians have to read and reduce their work intensity.

SUMMARY OF THE INVENTION

The present invention discloses a system and a method for a wireless capsule endoscope with an adaptive frame rate.

The frame rate of the capsule endoscope system is determined with a relative movement between the 6-axis sensor inside the capsule and the 6-axis sensor inside the portable recorder. Determination according to the relative movement allows the system to accurately locate the capsule and adjust the frame rate in real time, so as to reduce the repeats of images captured and the probability of missing lesions and improve the operating efficiency of the capsule endoscope.

To solve the above technical problems, the present invention discloses a system for a wireless capsule endoscope with an adaptive frame rate, which comprises a capsule endoscope which includes a capsule data processor and a first 6-axis sensor, and a portable recorder which includes a second 6-axis sensor and a recorder data processor.

The first 6-axis sensor is configured to collect the first posture information for the capsule endoscope; wherein the posture information is substantially an information about orientation.

The second 6-axis sensor is configured to collect the second posture information for the portable recorder.

The recorder data processor is configured to filter the first posture information and the second posture information to obtain a quaternion $p_0$ of the first posture information and a quaternion $p_1$ of the second posture information, and to calculate an interpolated median $s_0$ between $p_0$ and $p_1$ at time $t_0$, and an interpolated median $s_1$ between $p'_0$ and $p'_1$ at time $t_1$;

The recorder data processor is also configured to calculate a difference $diff_0$ between the interpolated median $s_0$ and $s_1$, and work out the dot product of the difference $diff_0$ and unit quaternion $[1, 0, 0, 0]$. If the result of the dot product calculation $|diff_0 \cdot [1,0,0,0]|^2 \in (0.01,1]$, it is determined that there is relative movement between the capsule endoscope and the portable recorder; otherwise there is no relative movement between the capsule endoscope and the portable recorder. According to the determination, a corresponding command signal is generated and transmitted to the capsule endoscope; and The capsule data processor is configured to receive a command signal transmitted by the portable recorder, and the frame rate of the capsule endoscope is adjusted according to the command signal.

As a further improvement of the present invention, if it is determined from the command signal that there is relative movement between the capsule endoscope and the portable recorder, the frame rate of the capsule endoscope is adjusted as follows:

The recorder data processor transmits the result as a command signal to the capsule data processor;

When there is a relative movement between the capsule endoscope and the portable recorder, the capsule data processor collects the current rate value of the camera unit; if the current rate of the camera unit reaches the maximum value, an adjustment is not needed; otherwise the frame rate of the camera unit is increased by the capsule data processor.

When there is no relative movement between the capsule endoscope and the portable recorder, the frame rate of the camera unit is reduced by the capsule data processor.

As a further improvement of the present invention, if the command signal is a signal used to adjust the frame rate of the camera unit, the frame rate of the capsule endoscope is adjusted as follows:

When there is a relative movement between the capsule endoscope and the portable recorder, the recorder data processor gets the current frame rate value of the camera unit.

If the current frame rate of the camera unit reaches the maximum value, a command signal for not adjusting the frame rate is transmitted to the capsule data processor; otherwise a command signal for increasing the frame rate of the camera unit is transmitted to the capsule data processor.

When there is no relative movement between the capsule endoscope and the portable recorder, a command signal for reducing the frame rate of the camera unit is transmitted to the capsule data processor.

According to the received command signal, the frame rate of the capsule endoscope is adjusted with the capsule data processor, to increase the frame rate.

The present invention discloses a method for frame rate adaptation based on a wireless capsule endoscope system, comprising the following steps:

Step 1: The first 6-axis sensor collects the first posture information of the capsule endoscope; the second 6-axis sensor collects the second posture information for the portable recorder;

Step 2: The recorder data processor filters the first posture information and the second posture information to obtain a quaternion $p_0$ of the first posture information and a quaternion $p_1$ of the second posture information to calculate an interpolated median $s_0$ between $p_0$ and $p_1$ at time $t_0$, and an interpolated median $s_1$ between $p'_0$ and $p'_1$ at time $t_1$;

Step 3: The recorder data processor calculates a difference $diff_0$ between the interpolated median $s_0$ and $s_1$, and works out the dot product of the difference $diff_0$ and unit quaternion [1, 0, 0, 0]. If the result of the dot product calculation $|diff_0 \cdot [1,0,0,0]|^2 \in (0.01, 1]$, it is determined that there is relative movement between the capsule endoscope and the portable recorder; otherwise there is no relative movement between the capsule endoscope and the portable recorder. According to the determination, a corresponding command signal is generated and transmitted to the capsule endoscope.

The capsule data processor receives a command signal transmitted by the portable recorder, and adjusts the frame rate of the capsule endoscope according to the command signal.

Compared with prior art, the present invention delivers the following beneficial effects:

The capsule endoscope system with the adaptive frame rate disclosed herein determines whether to adjust the image frame rate according to the relative movement between the 6-axis sensors, which can effectively reduce the possibility of taking too many images at the same position and missing lesions when the capsule moves too fast so as to improve the operating efficiency of the capsule and effectively avoid taking a large number of repetitive and redundant photos.

The present invention can obtain the actual movement rate of the capsule more exactly by determining the position of the capsule by relative movement, so that the capsule endoscope can be controlled more accurately.

The present invention, depending on measurement of relative motion, can effectively avoid capsule misjudgment caused by a small movements of the human body and improve the accuracy of gastrointestinal motility.

The present invention provides an adaptive adjustment for frame rates of the capsule endoscope, and can adaptively control the frame rate of the capsule in the human digestive tract according to its position and motion state.

Wherein, 1—Capsule endoscope, 1.1—Internal power supply unit, 1.2—Camera unit, 1.3—First RF transmission device, 1.4—Capsule data processor, 1.5—First 6-axis sensor, 2—Portable recorder, 2.1—Second RF transmission device, 2.2—Second 6-axis sensor, 2.3—Recorder data processor.

DETAILED DESCRIPTION OF THE PREFERRED EMBODIMENTS

The present invention is herein described, by way of preferred embodiments, with reference to accompanying drawings.

Figure 1:
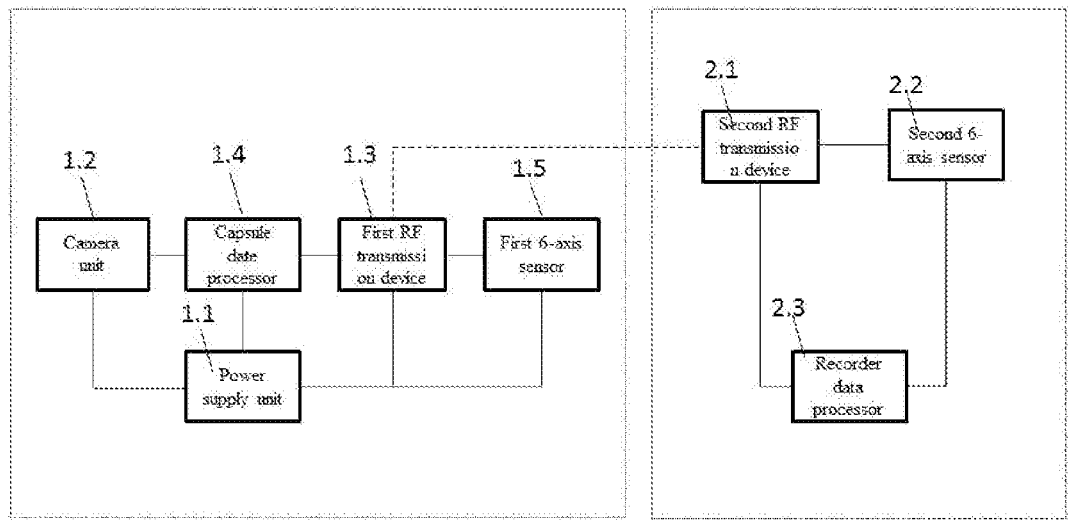
FIG. 1 shows a structural view of a wireless capsule endoscope system according to the present invention.

The present invention discloses a wireless capsule endoscope system with an adaptive frame rate, as shown in FIG. 1, comprising a capsule endoscope 1 and a portable recorder 2. The capsule endoscope 1 comprises an internal power supply unit 1.1, a camera unit 1.2, a first RF transmission device 1.3, a capsule data processor 1.4 and a first 6-axis sensor 1.5. The portable recorder 2 comprises a second RF transmission device 2.1, a second 6-axis sensor 2.2 and a recorder data processor 2.3.

The signal output port of the camera unit 1.2 is connected to the image signal input port of the capsule data processor 1.4, the data communication port of the capsule data processor 1.4 is connected to the first RF communication port of the first RF transmission device 1.3, the signal output port of the first 6-axis sensor 1.5 is connected to the second RF communication port of the first RF transmission device 1.3, the third communication port of the first RF transmission device 1.3 is wirelessly connected by RF signal to the first communication port of the second RF transmission device 2.1, the signal output port of the second 6-axis sensor 2.2 is connected to the first data communication port of the recorder data processor 2.3, and the second data communication port of the recorder data processor 2.3 is connected to the second communication port of the second RF transmission device 2.1.

The first 6-axis sensor 1.5 is configured to collect a first posture information of the capsule endoscope 1; the second 6-axis sensor 2.2 is configured to collect a second posture information of the portable recorder 2. The portable recorder 2 is fixed to a position outside the subject, such as the abdomen, by a belt or a vest or the like at the time of use. The posture information collected by the first 6-axis sensor 1.5 is transmitted to the recorder data processor 2.3 through the first RF transmission device 1.3 and the second RF transmission device 2.1.

The recorder data processor 2.3 is configured to receive the first posture information collected by the first 6-axis sensor 1.5 and the second posture information collected by the second 6-axis sensor 2.2, and determine whether or not there is a relative movement between the capsule endoscope 1 and the portable recorder 2 according to the first posture information and the second posture information. According to the determination result, a corresponding command signal is generated and transmitted to the capsule endoscope 1. The capsule data processor 1.4 is configured to receive a command signal transmitted by the portable recorder 2, and adjust the frame rate of the capsule endoscope 1 according to the command signal. The command signal may be the result of a determination of whether or not there is a relative movement between the capsule endoscope 1 and the portable recorder 2. At this point, the capsule data processor 1.4 collects the current image frame rate value of the camera unit 1.2 and adjusts the frame rate of the capsule endoscope 1 according to the command signal and the current image frame rate value collected. In addition, the command signal may also be a signal for adjusting the image frame rate of the camera unit 1.2; that is, the recorder data processor 2.3 gets the current image frame rate value of the camera unit 1.2 and generates a signal for adjusting the image frame rate of the capsule endoscope 1 according to the command signal and the current frame rate value collected.

In the preferred embodiment of the present invention, the recorder data processor 2.3 determines whether there is a relative movement between the capsule endoscope 1 and the portable recorder 2 by the following steps: filter the first posture information of the capsule endoscope 1 and the second posture information of the portable recorder 2 with a filter fusion algorithm to obtain a quaternion $p_0$ of the first posture information and a quaternion $p_1$ of the second posture information; both of the quaternion $p_0$ of the first posture information and the quaternion $p_1$ of the second posture information represent a four-dimensional space vector of posture information; calculate an interpolated median $s_0$ between $p_0$ and $p_1$ at time $t_0$, and an interpolated median $s_1$ between $p'_0$ and $p'_1$ at time $t_1$; calculate a difference $diff_0$ between the interpolated median $s_0$ and $s_1$, and work out the dot product of the difference $diff_0$ and unit quaternion [1, 0, 0, 0]. If the result of the dot product calculation $|diff_0 \cdot [1,0, $0,0]|^2 \in (0.01,1]$, it is determined that there is a relative movement between the capsule endoscope 1 and the portable recorder 2; otherwise there is no relative movement between the capsule endoscope 1 and the portable recorder 2. In the preferred embodiment of the present invention, the $diff_0$ is calculated by $diff_0 = s_0^{-1} s_1$.

In the preferred embodiment of the present invention, if the command signal demonstrates that there is relative movement between the capsule endoscope 1 and the portable recorder 2, the frame rate of the capsule endoscope 1 is adjusted as follows: The recorder data processor 2.3 transmits the result as a command signal to the capsule data processor 1.4. When there is relative movement between the capsule endoscope 1 and the portable recorder 2, the capsule data processor 1.4 collects the current frame rate value of the camera unit 1.2. If the current frame rate of the camera unit 1.2 reaches the maximum value, an adjustment is not needed; otherwise if not at maximum value the image frame rate of the camera unit 1.2 is increased by the capsule data processor 1.4; when there is no relative movement between the capsule endoscope 1 and the portable recorder 2, the image frame rate of the camera unit 1.2 is reduced by the capsule data processor 1.4.

In the preferred embodiment of the present invention, if the command signal is a signal used to adjust the image frame rate of the camera unit 1.2, the frame rate of the capsule endoscope 1 is adjusted as follows: When there is a relative movement between the capsule endoscope 1 and the portable recorder 2, the recorder data processor 2.3 gets the current frame rate value of the camera unit 1.2; if the current frame rate of the camera unit 1.2 is at the maximum value, a command signal for not adjusting the frame rate is transmitted to the capsule data processor 1.4; otherwise a command signal for increasing the image frame rate of the camera unit 1.2 is transmitted to the capsule data processor 1.4. When there is no relative movement between the capsule endoscope 1 and the portable recorder 2, a command signal for reducing the image frame rate of the camera unit 1.2 is transmitted to the capsule data processor 1.4. According to the received command signal, the frame rate of the capsule endoscope 1 is adjusted with the capsule data processor 1.4.

Adjustments carried out to the frame rate of the capsule endoscope 1 according to the command signal include: When the command signal is not to adjust the frame rate, the capsule data processor 1.4 does not adjust the frame rate of the capsule endoscope 1, that is, maintains the current frame rate; when the command signal is to increase the frame rate of the camera unit 1.2, the capsule data processor 1.4 increases the frame rate of the capsule endoscope 1; when the command signal is to reduce the frame rate of the camera unit 1.2, the capsule data processor 1.4 reduces the frame rate of the capsule endoscope 1.

In the preferred embodiment of the present invention, the camera unit 1.2 is used to capture video images which are images in the body of the examinee, and the examinee may be a human being, an animal, or a digestive tract bionic model.

In the preferred embodiment of the present invention, the first posture information collected by the first 6-axis sensor 1.5 and the second posture information collected by the second 6-axis sensor 2.2 are synchronous.

In the preferred embodiment of the present invention, the camera unit 1.2, the first RF transmission device 1.3, the capsule data processor 1.4 and the first 6-axis sensor 1.5 are powered by the power supply unit 1.1 inside the capsule.

In the preferred embodiment of the present invention, the first 6-axis sensor 1.5 transmits the first posture information collected to the recorder data processor 2.3 via the first RF transmission device 1.3 and the second RF transmission device 2.1. The recorder data processor 2.3 solves the first posture information using a Mahony filter fusion algorithm and obtains a normalized quaternion of the first posture information; the second 6-axis sensor 2.2 transmits the second posture information collected to the recorder data processor 2.3. The recorder data processor 2.3 solves the second posture information using a Mahony filter fusion algorithm and obtains a normalized quaternion of the second posture information.

In the preferred embodiment of the present invention, when there is relative movement between the capsule endoscope 1 and the portable recorder 2, the capsule data processor 1.4 collects the current frame rate value of the camera unit 1.2. If the current frame rate of the camera unit 1.2 is at the maximum value (e.g. 15 fps), an adjustment is not needed; otherwise the frame rate of the camera unit 1.2 is increased by the capsule data processor 1.4. The frame rate of the camera unit 1.2 is divided into multiple levels, and each level corresponds to a different frame rate, such as 4 levels (0.5 fps, 5 fps, 10 fps and 15 fps). When the capsule data processor increases the frame rate, the camera unit 1.2 increases the current frame rate up by one level to get a larger frame rate. For example, when the current frame rate is 5 fps, the camera unit 1.2 lifts it up to 15 fps.

In the preferred embodiment of the present invention, when there is no relative movement between the capsule endoscope 1 and the portable recorder 2, the frame rate of the camera unit 1.2 is reduced by the capsule data processor 1.4. When the capsule data processor 1.4 reduces the frame rate, the camera unit 1.2 lowers the frame rate down by one level to get a smaller frame rate. For example, if the current frame rate is 5 fps, the camera unit 1.2 reduces it to 0.5 fps. If the current frame rate is already at the minimum value (0.5 fps), an adjustment is not needed.

In the preferred embodiment of the present invention, the interpolated median $s_0$ between the quaternion $p_0$ of the first posture information and the quaternion $p_1$ of the second posture information at time $t_0$ is calculated by a formula $s_0 = p_0 + \tau(p_1 - p_0)$. In the formula, the "$\tau$" is a dimensionless coefficient. $\tau = 0.5$ represents the median, $\tau = 0.1$ closer to $p_0$ and $\tau = 0.9$ closer to $p_1$. Similarly, the interpolated median $s_1$ between the quaternion $p'_0$ of the first posture information and the quaternion $p'_1$ of the second posture information at time $t_1$ is calculated by a formula $s_1 = p'_0 + \tau(p'_1 - p'_0)$.

Figure 2:
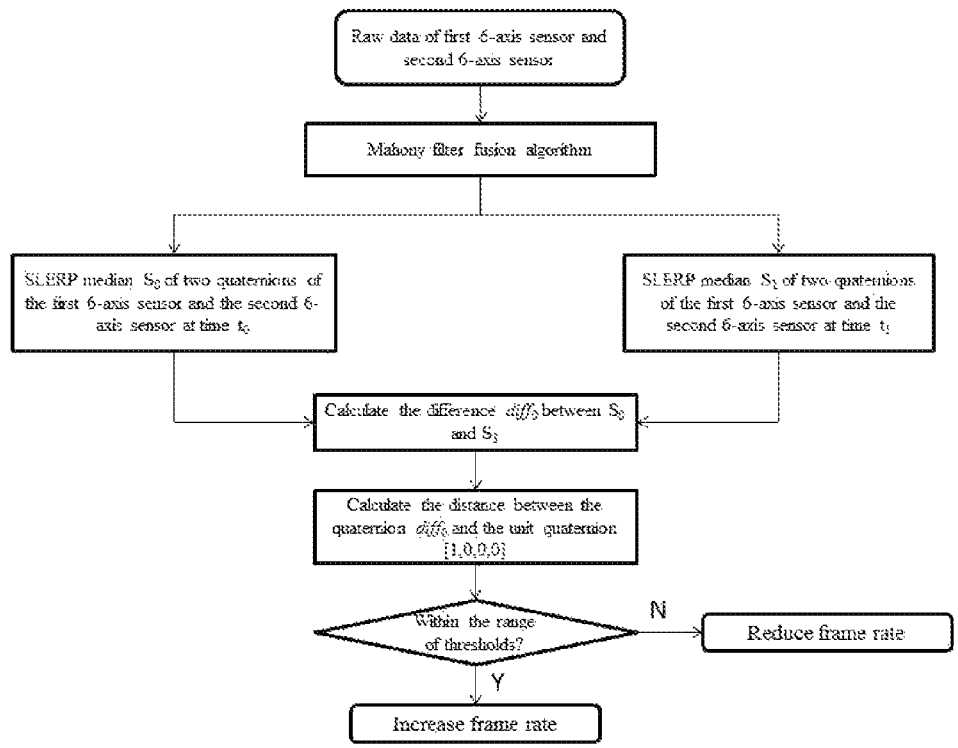
FIG. 2 shows a process flow diagram of the method for frame rate adaptation according to the present invention.

The present invention discloses a method for frame rate adaptation based on the wireless capsule endoscope system, as shown in FIG. 2, comprising the following steps:

Step 1: The first 6-axis sensor 1.5 collects a first posture information of the capsule endoscope 1; the second 6-axis sensor 2.2 collects a second posture information of the portable recorder 2;

Step 2: The first 6-axis sensor 1.5 and the second 6-axis sensor 2.2 transmit the first posture information and the second posture information to the recorder data processor 2.3. The recorder data processor 2.3 filters the first posture information and the second posture information with a filter fusion algorithm to obtain a quaternion $p_0$ of the first posture information and a quaternion $p_1$ of the second posture information, both of which represent a four-dimensional space vector of posture information, and to calculate an interpolated median $s_0$ between $p_0$ and $p_1$ at time $t_0$, and an interpolated median $s_1$ between $p'_0$ and $p'_1$ at time $t_1$;

Step 3: The recorder data processor 2.3 calculates a difference $diff_0$ between the interpolated median $s_0$ and $s_1$, and works out the dot product of the difference $diff_0$ and unit quaternion [1, 0, 0, 0]. If the result of the dot product calculation $|diff_0 \cdot [1,0,0,0]|^2 \in (0.01,1]$, it is determined that there is relative movement between the capsule endoscope 1 and the portable recorder 2, otherwise there is no relative movement between the capsule endoscope 1 and the portable recorder 2; when there is a relative movement between the capsule endoscope 1 and the portable recorder 2, the capsule data processor 1.4 collects the current frame rate value of the camera unit 1.2. If the current frame rate of the camera unit 1.2 is at the maximum value, an adjustment is not needed; otherwise the frame rate of the camera unit 1.2 is increased by the capsule data processor 1.4. When there is no relative movement between the capsule endoscope 1 and the portable recorder 2, the frame rate of the camera unit 1.2 is reduced by the capsule data processor 1.4.

According to the frame rate adjustment process disclosed herein, it is required to determine first whether the current frame rate is the maximum value. If not, and there is a relative movement determined according to the above calculation, the frame rate needs to be increased; if it is the maximum frame rate, maintain the current value; if it is determined according to the relative difference calculated that there is no relative movement between the capsule endoscope 1 and the portable recorder 2, the frame rate needs to be reduced and it should be reduced to 1 fps or less to avoid repetition of images captured until the next determination that there is relative movement. The adjustment process can be executed cyclically to realize a control of the frame rate adaptation to thereby control the frame rate and avoid the problem of relative position misalignment caused by the positioning of the capsule endoscope itself so that the frame rate can be adjusted more accurately and the operating efficiency of the capsule endoscope can be improved.

Although certain disclosed embodiments of the present disclosure have been specifically described, the present disclosure is not to be construed as being limited thereto.

Various changes or modifications may be made to the present disclosure without departing from the scope and spirit of the present disclosure.

What is claimed is:

1. A system for wireless capsule endoscope with an adaptive frame rate, comprising:
   a capsule endoscope (1) including a capsule data processor (1.4) and a first 6-axis sensor (1.5), and
   a portable recorder (2) including a second 6-axis sensor (2.2) and a recorder data processor (2.3), wherein:
   the first 6-axis sensor (1.5) is configured to collect a first posture information of the capsule endoscope (1);
   the second 6-axis sensor (2.2) is configured to collect a second posture information of the portable recorder (2);
   the recorder data processor (2.3) is configured to filter the first posture information and the second posture information to obtain a quaternion $p_0$ of the first posture information and a quaternion $p_1$ of the second posture information, and to calculate an interpolated median $s_0$ between $p_0$ and $p_1$ at time $t_0$, and an interpolated median $s_1$ between $p'_0$ and $p'_1$ at time $t_1$;
   the recorder data processor (2.3) is also configured to calculate a difference $diff\_0$ between the interpolated median $s_0$ and $s_1$, and work out the dot product of the difference $diff_0$ and unit quaternion [1, 0, 0, 0];
   if the result of the dot product calculation $|diff_0 \cdot [1,0,0,0]|^2 \in (0.01,1]$, the recorder data processor determines that there is a relative movement between the capsule endoscope (1) and the portable recorder (2), otherwise the recorder data processer determines that there is no relative movement between the capsule endoscope (1) and portable recorder (2);
   according to the determination, a corresponding command signal is generated and transmitted to the capsule endoscope (1) by the portable recorder (2); and
   the capsule data processor (1.4) is configured to receive the command signal transmitted by the portable recorder (2), and adjust frame rate of the capsule endoscope (1) according to the command signal.

2. The system of claim 1, wherein the frame rate of the capsule endoscope (1) is configured to be adjusted using the following steps:
   transmitting the result as a command signal to the capsule data processor (1.4) by the recorder data processor (2.3);
   when a relative movement between the capsule endoscope (1) and the portable recorder (2) is determined by the recorder data processor,
   collecting a current frame rate value of the camera unit (1.2) by the capsule data processor (1.4);
   if the current frame rate of the camera unit (1.2) reaches a maximum value, an adjustment is not performed, otherwise increasing the frame rate of the camera unit (1.2) by the capsule data processor (1.4); and
   when no relative movement between the capsule endoscope (1) and the portable recorder (2) is determined by the recorder data processor, reducing the frame rate of the camera unit (1.2) by the capsule data processor (1.4).

3. The system of claim 2, wherein the camera unit (1.2) has multiple possible frame rates, called levels;
   when the capsule data processor (1.4) increases the frame rate, the camera unit (1.2) increases frame rate to the next higher level to get a higher frame rate.

4. The system of claim 2, wherein the camera unit (1.2) has multiple possible frame rates, called levels;
   when the frame rate is reduced via the capsule data processor (1.4), the camera unit (1.2) reduces the frame rate to the next lower level to get a lower frame rate, wherein if the current frame rate is already at a minimum value, a downward adjustment of the frame rate does not occur.

5. The system of claim 1, wherein the frame rate of the capsule endoscope (1) is configured to be adjusted using the following steps:
   when a relative movement between the capsule endoscope (1) and the portable recorder (2) is determined by the recorder data processor (2.3), the recorder data processor (2.3) gets the current frame rate value of the camera unit (1.2);
   if the current frame rate of the camera unit (1.2) reaches a maximum value, transmitting a command signal for not adjusting the frame rate to the capsule data processor (1.4) by the recorder data processor (2.3), otherwise transmitting a command signal for increasing the frame rate of the camera unit (1.2) to the capsule data processor (1.4) by the recorder data processor (2.3);
   when no relative movement between the capsule endoscope (1) and the portable recorder (2) is determined by the recorder data processor (2.3), transmitting a command signal for reducing the frame rate of the camera unit (1.2) to the capsule data processor (1.4) by the recorder data processor (2.3); and after receiving the command signal, adjusting the frame rate of the capsule endoscope (1) by the capsule data processor (1.4) according to the signal.

6. The system of claim 1, wherein the first posture information collected by the first 6-axis sensor (1.5) and the second posture information collected by the second 6-axis sensor (2.2) are synchronous.

7. The system of claim 1, wherein the capsule endoscope (1) further comprises a first RF transmission device (1.3), and the portable recorder (2) further comprises a second RF transmission device (2.1):

the first 6-axis sensor (1.5) transmits the first posture information collected to the recorder data processor (2.3) via the first RF transmission device (1.3) and the second RF transmission device (2.1); and the second 6-axis sensor (2.2) transmits the second posture information collected to the recorder data processor (2.3).

8. The system of claim 1, wherein the recorder data processor (2.3) solves the first posture information using Mahony filter fusion algorithm, and obtains a normalized quaternion of the first posture information;

the recorder data processor (2.3) also solves the second posture information using Mahony filter fusion algorithm, and obtains a normalized quaternion of the second posture information.

9. The system of claim 1, wherein the interpolated median $s_0$ between the quaternion $p_0$ of the first posture information and the quaternion $p_1$ of the second posture information at time $t_0$ is calculated by a formula $s_0 = p_0 + \tau(p_1 - p_0)$; the interpolated median $s_1$ between the quaternion $p'_0$ of the first posture information and the quaternion $p'_1$ of the second posture information at time $t_1$ is calculated by a formula $s_1 = p'_0 + \tau(p'_1 - p'_0)$.

10. A method for frame rate adaptation using the wireless capsule endoscope system of claim 1, comprising the following steps:

step 1: the first 6-axis sensor (1.5) collects a first posture information of the capsule endoscope (1);

the second 6-axis sensor (2.2) collects a second posture information of the portable recorder (2);

step 2: the recorder data processor (2.3) filters the first posture information and the second posture information to obtain a quaternion $p_0$ of the first posture information and a quaternion $p_1$ of the second posture information, and to calculate an interpolated median $s_0$ between $p_0$ and $p_1$ at time $t_0$, and an interpolated median $s_1$ between $p'_0$ and $p'_1$ at time $t_1$;

step 3: the recorder data processor (2.3) calculates a difference $\text{diff}_0$ between the interpolated median $s_0$ and $s_1$, and works out the dot product of the difference $\text{diff}_0$ and unit quaternion $[1, 0, 0, 0]$;

if the result of the dot product calculation $|\text{diff}_0 \cdot [1,0,0,0]|^2 \in (0.01, 1]$, a relative movement between the capsule endoscope (1) and the portable recorder (2) is determined by the recorder data processor, otherwise there is no relative movement between the capsule endoscope (1) and the portable recorder (2) is determined by the recorder data processor according to the determination, a corresponding command signal is generated and transmitted to the capsule endoscope (1);

the capsule data processor (1.4) receives the command signal transmitted by the portable recorder (2), and adjusts frame rate of the capsule endoscope (1) according to the command signal.

* * * * *